United States Patent
Onozawa

(10) Patent No.: US 11,297,272 B2
(45) Date of Patent: Apr. 5, 2022

(54) SOLID-STATE IMAGING DEVICE AND ENDOSCOPIC CAMERA

(71) Applicant: NUVOTON TECHNOLOGY CORPORATION JAPAN, Kyoto (JP)

(72) Inventor: Kazutoshi Onozawa, Osaka (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 0 days.

(21) Appl. No.: 17/124,171

(22) Filed: Dec. 16, 2020

(65) Prior Publication Data

US 2021/0105428 A1 Apr. 8, 2021

Related U.S. Application Data

(63) Continuation of application No. PCT/JP2019/024089, filed on Jun. 18, 2019.

(30) Foreign Application Priority Data

Jun. 20, 2018 (JP) .............................. JP2018-117451

(51) Int. Cl.
*H04N 5/374* (2011.01)
*H04N 5/378* (2011.01)
(Continued)

(52) U.S. Cl.
CPC ........... *H04N 5/3745* (2013.01); *H04N 5/347* (2013.01); *H04N 5/378* (2013.01); *H04N 2005/2255* (2013.01)

(58) Field of Classification Search
CPC ...... H04N 5/3745; H04N 5/347; H04N 5/378; H04N 2005/2255; H04N 5/232;
(Continued)

(56) References Cited

U.S. PATENT DOCUMENTS

2008/0079806 A1* 4/2008 Inuiya ................ H04N 9/04557
348/65
2009/0062612 A1* 3/2009 Suda ....................... H04N 5/232
600/118
(Continued)

FOREIGN PATENT DOCUMENTS

JP 2011-104000 A 6/2011
JP 2017-184198 A 10/2017

OTHER PUBLICATIONS

International Search Report and Written Opinion dated Sep. 10, 2019 in International Application No. PCT/JP2019/024089; with partial English translation.

*Primary Examiner* — Marly S Camargo
(74) *Attorney, Agent, or Firm* — McDermott Will & Emery LLP

(57) ABSTRACT

A solid-state imaging device includes: a first semiconductor substrate including a light receiver that receives incident light; and a second semiconductor substrate including an image processing circuit that processes a signal from the light receiver and generates an image signal. The second semiconductor substrate includes: a nonvolatile memory including a region in which use history data is stored; and a control circuit (use history securing circuit) that restricts output of the image signal when the use history data is stored in the nonvolatile memory.

6 Claims, 7 Drawing Sheets

(51) Int. Cl.
    *H04N 5/225*     (2006.01)
    *H04N 5/232*     (2006.01)
    *A61B 1/005*     (2006.01)
    *A61B 1/012*     (2006.01)
    *G02B 23/24*     (2006.01)
    *H04N 5/3745*     (2011.01)
    *H04N 5/347*     (2011.01)

(58) Field of Classification Search
    CPC ........ H04N 5/343; H04N 5/379; H04N 5/225; H04N 5/23212; A61B 1/00002; A61B 1/00011; A61B 1/0125; A61B 1/00052; A61B 1/00059; A61B 1/051; A61B 1/00188; A61B 1/00006; A61B 1/005; G02B 23/24; G02B 23/2415
    USPC ..... 348/294, 297, 308, 301, 302, 45, 65, 72, 348/74, 686; 257/291, 292, 293, 443, 28, 257/37; 250/208.1; 600/118, 101, 104, 600/109, 117, 132, 145, 920
    See application file for complete search history.

(56) References Cited

U.S. PATENT DOCUMENTS

| | | | |
|---|---|---|---|
| 2016/0336262 A1* | 11/2016 | Yamashita | H01L 23/498 |
| 2017/0265728 A1* | 9/2017 | Ichikawa | A61B 1/00188 |
| 2019/0104251 A1 | 4/2019 | Otsuki et al. | |
| 2020/0314368 A1* | 10/2020 | Tsukuda | H04N 5/3598 |
| 2021/0368086 A1* | 11/2021 | Talbert | H04N 5/332 |

* cited by examiner

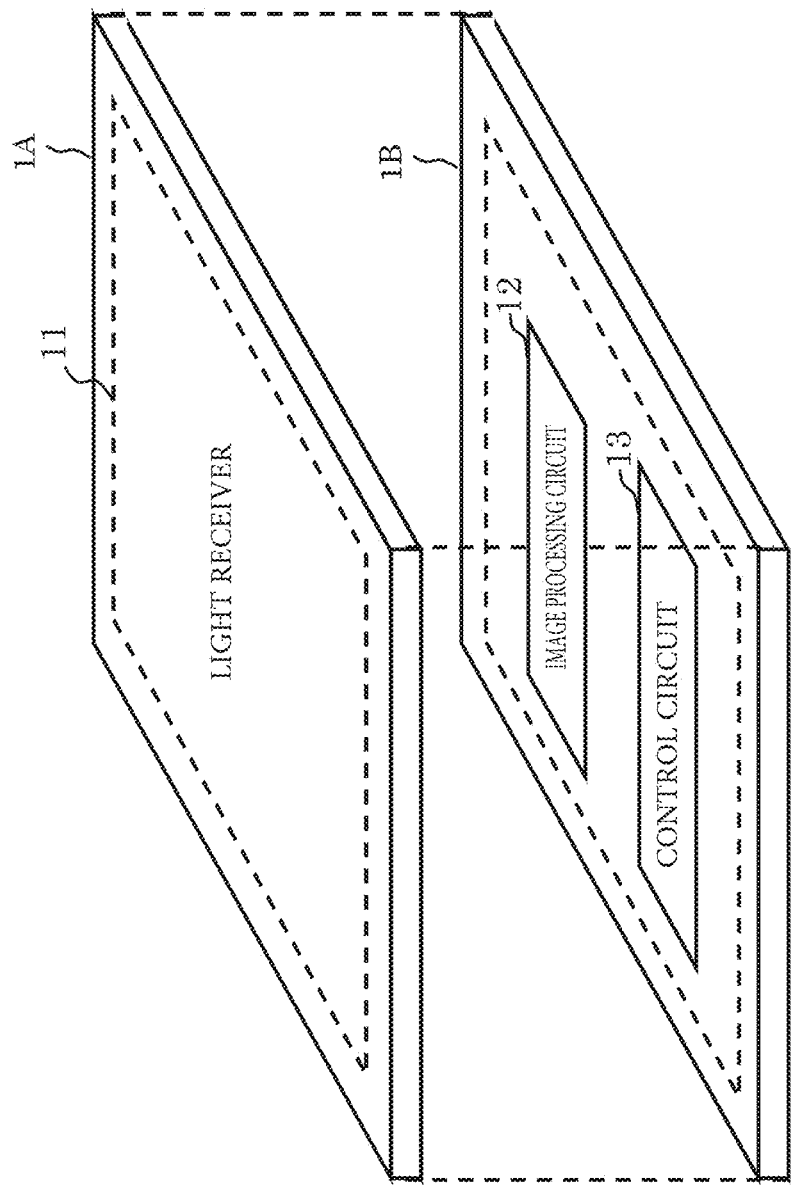

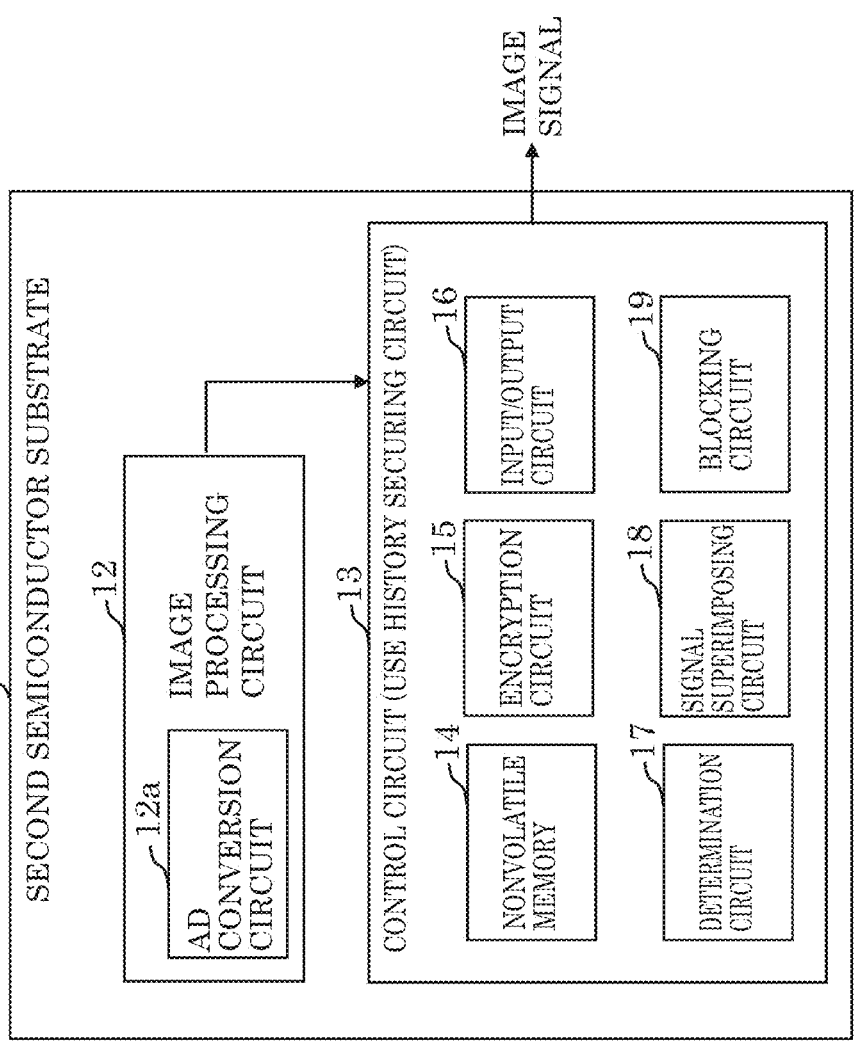

SOLID-STATE IMAGING DEVICE AND ENDOSCOPIC CAMERA

CROSS REFERENCE TO RELATED APPLICATIONS

This application is a U.S. continuation application of PCT International Patent Application Number PCT/JP2019/024089 filed on Jun. 18, 2019, claiming the benefit of priority of Japanese Patent Application Number 2018-117451 filed on Jun. 20, 2018, the entire contents of which are hereby incorporated by reference.

BACKGROUND

1. Technical Field

The present disclosure relates to a solid-state imaging device and an endoscopic camera.

2. Description of the Related Art

The following describes a conventional solid-state imaging device disclosed in Patent Literature 1 (Japanese Unexamined Patent Application Publication No. 2017-184198) with reference to a drawing. FIG. 6 is a block diagram of a configuration of the conventional solid-state imaging device.

As in FIG. 6, solid-state imaging device 120 includes signal processing substrate 123 arranged on the back side of pixel substrate 122 and is stacked in two layers. Pixel substrate 122 includes sensor unit 121 that photoelectrically converts optical signals from an object into electric signals. Signal processing substrate 123 includes image information processing unit 104 and image information output unit 124.

Image information processing unit 104 includes at least analog/digital conversion unit (A/D conversion unit) 125 that converts the electrical signals output from sensor unit 121, which are analog signals, into digital signals and integrated-information forming unit 126 that forms integrated information in which image information obtained by A/D conversion unit 125 and image sensor identification information of solid-state imaging device 120 are associated with each other.

Image information output unit 124 outputs the image information output from A/D conversion unit 125 and the integrated information output from integrated-information forming unit 126 to the external unit.

With this configuration, the solid-state imaging device in Patent Literature 1 guarantees consistency between acquired image information and picked-up image information.

SUMMARY

Use of a disposable solid-state imaging device has been sometimes required recently, for example, in a medical setting, instead of using a solid-state imaging device (or a camera, for example, an endoscopic camera equipped with a solid-state imaging device) that is asepticized to be usable again after each time a checkup or a surgery is performed. For example, a disposable solid-state imaging device is packaged and delivered to a hospital.

However, the solid-state imaging device disclosed in the conventional technique is not suitable for disposable use. For example, even if the conventional solid-state imaging device is used as a disposable device, the solid-state imaging device can be used after the solid-state imaging device is used once. The solid-state imaging device may be reused by mistake, for example.

The present disclosure has been conceived in view of the above problem, and aims to provide a solid-state imaging device and an endoscopic camera that are suitable for disposable use and hardly reused.

In order to solve the above problem, a solid-state imaging device according to one aspect of the present disclosure includes: a first semiconductor substrate including a light receiver that receives incident light; and a second semiconductor substrate including an image processing circuit that processes a signal from the light receiver and generates an image signal. The second semiconductor substrate includes: a nonvolatile memory including a region in which use history data is stored; and a control circuit that restricts output of the image signal when the use history data is stored in the nonvolatile memory.

Moreover, an endoscopic camera according to one aspect of the present disclosure includes the solid-state imaging device described above.

The solid-state imaging device and the endoscopic camera according to one aspect of the present disclosure are suitable for disposable use.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

FIG. 3 is a diagram of an exemplary configuration of the solid-state imaging device according to Embodiment 1;

FIG. 4 is a diagram of an exemplary configuration of a second semiconductor substrate of the solid-state imaging device according to Embodiment 1:

DETAILED DESCRIPTION OF THE EMBODIMENT

The following further specifically describes an embodiment according to the present disclosure with reference to the drawings.

Note that the embodiment described below shows a general or specific example. The numerical values, shapes, structural elements, the arrangement and connection of the structural elements, etc. shown in the following embodiments are mere examples, and do not limit the present disclosure. Of the structural elements in the following embodiments, structural elements not recited in any one of the independent claims representing broadest concepts are described as optional structural elements.

Embodiment 1

Figure 1:
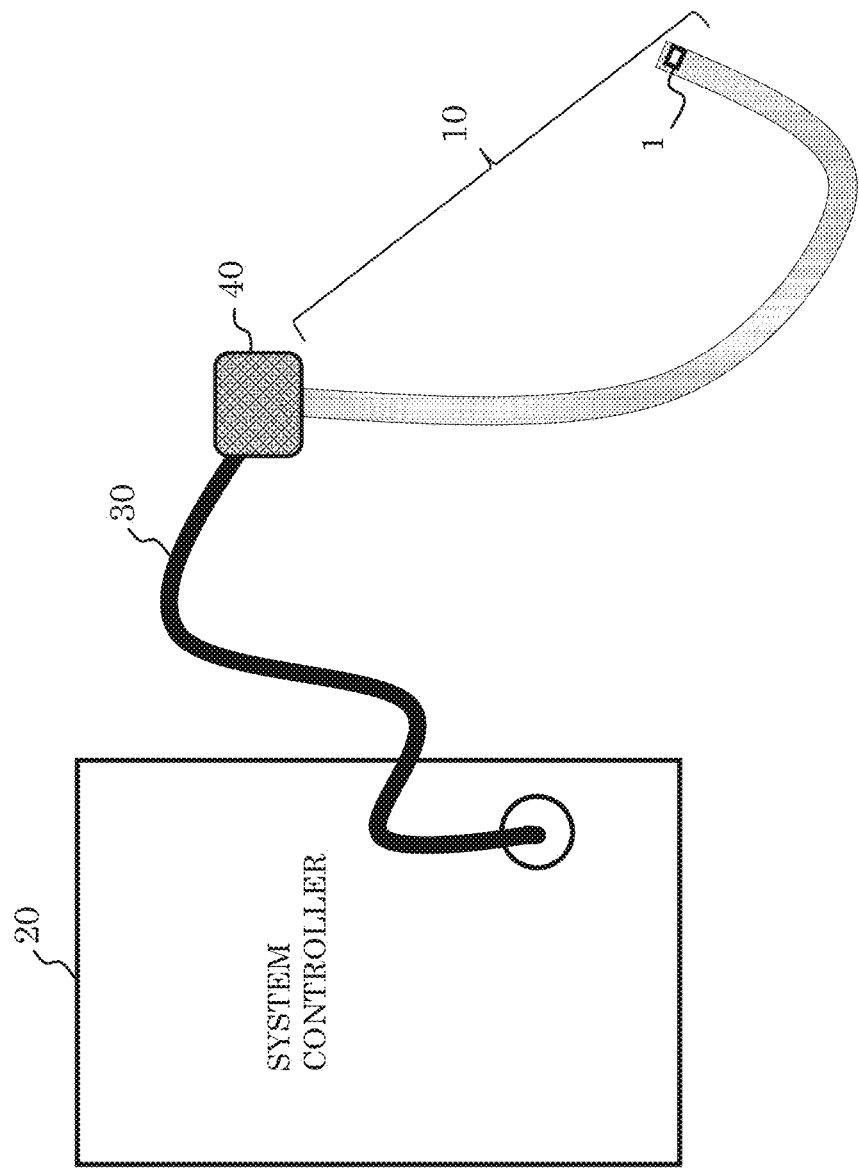
FIG. 1 is a block diagram of an exemplary configuration of an endoscopic camera system including a solid-state imaging device according to Embodiment 1.

FIG. 1 is a block diagram of an exemplary configuration of endoscopic camera system 100 including a solid-state imaging device.

Endoscopic camera system 100 includes at least camera scope 10 and system controller 20. Camera scope 10 performs observation during a checkup or a surgery. System controller 20 processes an observation image and controls camera scope 10. In endoscopic camera system 100 in FIG. 1, camera scope 10 is connected to system controller 20 via cable 30. Cable 30 includes scope controller 40. System controller 20 includes a monitor on which observation is performed during a checkup or a surgery, and an information input device.

Figure 2:
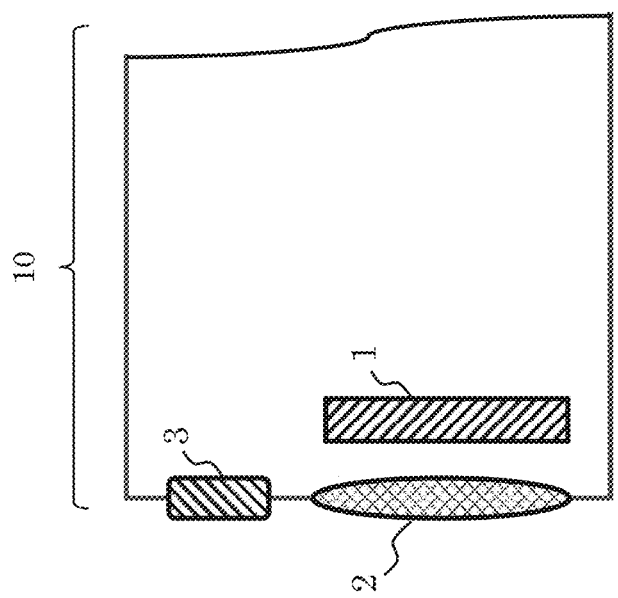
FIG. 2 is a diagram of an exemplary configuration of an end portion of a camera scope according to Embodiment 1.

Camera scope 10 corresponds to a disposable camera (endoscopic camera). FIG. 2 is a diagram of an exemplary configuration of an end portion of camera scope 10. The end portion of camera scope 10 includes solid-state imaging device 1, imaging lens 2, and illumination light source 3, for example. Camera scope 10 is disposed of in a predetermined way without being reused when camera scope 10 is used once. Camera scope 10 is a disposable sterile scope (i.e., endoscopic camera) and attached to cable 30. Camera scope 10 is disposed of after a checkup or a surgery.

Cable 30 is connected to system controller 20.

Cable 30 includes scope controller 40 that controls operations of camera scope 10. Scope controller 40 outputs a control signal to each circuit, such as solid-state imaging device 1 and illumination light source 3.

FIG. 3 is a diagram of an exemplary configuration of solid-state imaging device 1 according to Embodiment 1. Solid-state imaging device 1 in FIG. 3 includes first semiconductor substrate 1A and second semiconductor substrate 1B. First semiconductor substrate 1A includes light receiver 11 on the front surface. Second semiconductor substrate 1B includes image processing circuit 12 and control circuit 13. Control circuit 13 is also referred to as a use history securing circuit. Light emitted from illumination light source 3 illuminates an observation part. Light reflected off the observation part passes through imaging lens 2, and reaches light receiver 11 in which unit cells (pixel cells) including photoelectric converters (pixels, as an example, photodiodes) are arranged in a two-dimensional array. Photoelectric converters photoelectrically convert incident light on first semiconductor substrate 1A of solid-state imaging device 1 illustrated in FIG. 3. Accordingly, a signal corresponding to the amount of light is generated. Next, after the signal is transmitted to second semiconductor substrate 1B, the signal is converted into a digital signal by AD conversion circuit 12a. The image signal converted into a digital signal is input to control circuit 13 (use history securing circuit) of second semiconductor substrate 1B.

FIG. 4 is a diagram of an exemplary configuration of second semiconductor substrate 1B of the solid-state imaging device according to Embodiment 1. As illustrated in FIG. 4, second semiconductor substrate 1B includes image processing circuit 12 and control circuit 13. Image processing circuit 12 includes AD conversion circuit 12a. Control circuit 13 includes nonvolatile memory 14, encryption circuit 15, input/output circuit 16, determination circuit 17, signal superimposing circuit 18, and blocking circuit 19.

In nonvolatile memory 14, a unique identification (ID) of solid-state imaging device 1 is written. Moreover, nonvolatile memory 14 includes a region in which use history data is stored. When camera scope 10 is used for the first time, for example, information about the image capturing device (image capturing device information); and date and time of image capturing are written in nonvolatile memory 14 as the use history data. The image capturing device information and the date and time of image capturing are transmitted from system controller 20.

The image capturing device information; the date and time of image capturing; and the identification (ID), which are stored in nonvolatile memory 14, are encrypted as a use history information group by encryption circuit 15, and superimposed on the image signal by signal superimposing circuit 18. At this time, signal superimposing circuit 18 may superimpose the use history information group on a part other than effective pixels in the image signal, and may superimpose the use history information group on a part in the effective pixels in the image signal as a digital watermark. Accordingly, the image signal is output on which the encrypted ID, image capturing device information, and date and time of image capturing, for example, are superimposed. This prevents a misdiagnosis due to a mistake, such as referring to wrong image data obtained by capturing a subject, and also prevents forgery and falsification.

Camera scope 10 is removed and disposed of after a checkup or a surgery. When camera scope 10 is connected to cable 30 again by mistake, determination circuit 17 in the use history securing circuit determines whether a use history information group is present in nonvolatile memory 14, and when a use history is present, the image signal is blocked by blocking circuit 19. For example, blocking circuit 19 prohibits output of the image signal from input/output circuit 16. This ensures that the disposable image capturing device is appropriately used and will not be reused.

Note that blocking circuit 19 may restrict output of the image signal instead of blocking the image signal (i.e., prohibiting output of the entire image signal). For example, blocking circuit 19 may prohibit output of a part in effective pixels in the image signal, or may replace the part in the effective pixels with specific image data. Such specific image data may be, for example, image data showing a blue image, or a message image indicating "used".

Solid-state imaging device 1 according to the present embodiment includes first semiconductor substrate 1A that includes light receiver 11 that receives incident light from an imaging optical system, and second semiconductor substrate 1B that includes image processing circuit 12 that processes a signal from light receiver 11. First semiconductor substrate 1A and second semiconductor substrate 1B are stacked and joined together.

Figure 5A:
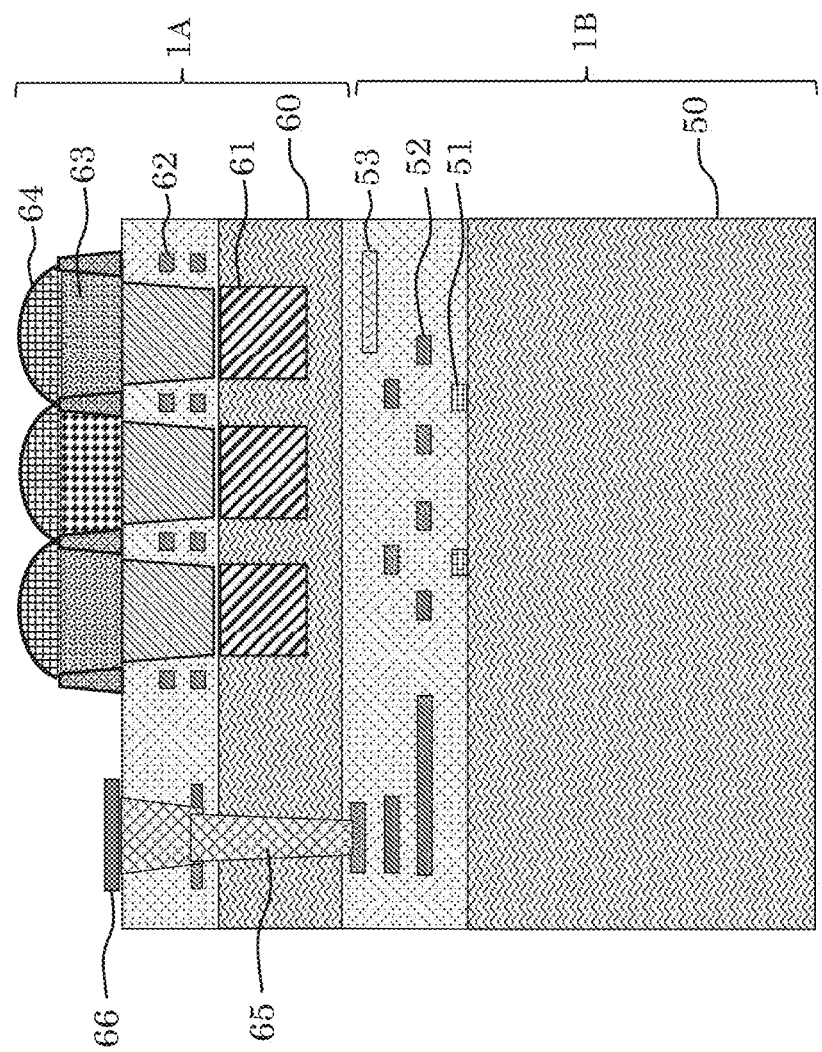
FIG. 5A is a cross-sectional view of an example of a stacked chip representing the solid-state imaging device according to Embodiment 1.
Figure 5B:
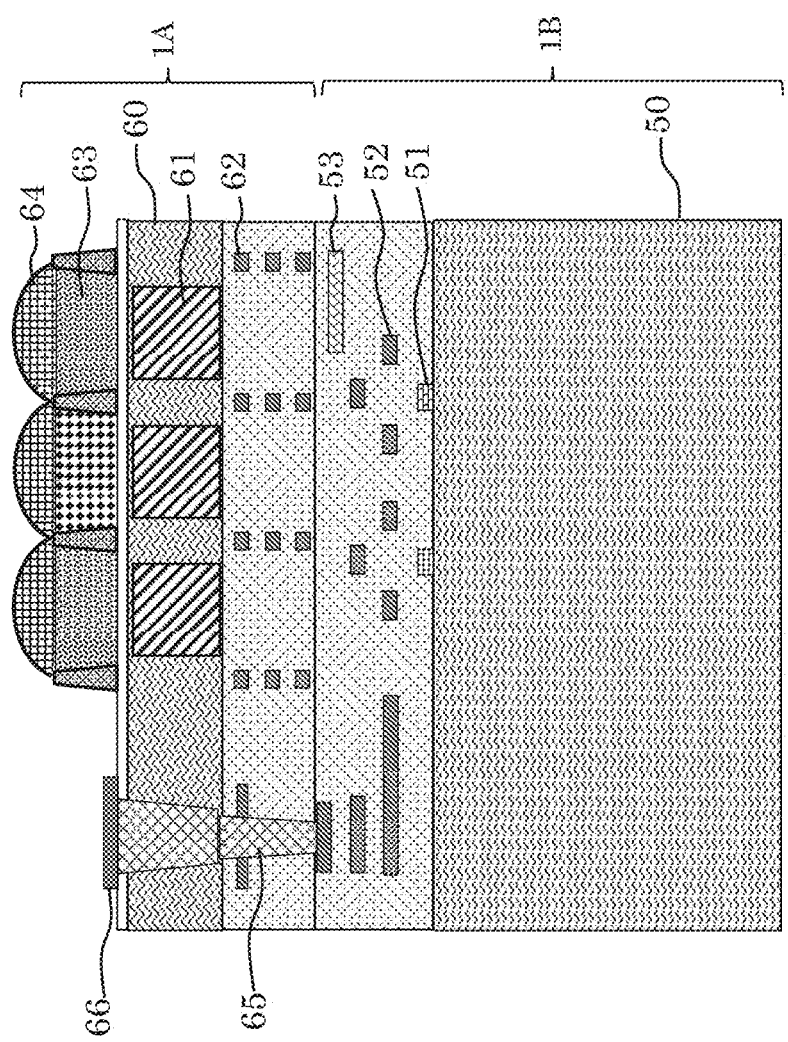
FIG. 5B is a cross-sectional view of another example of a stacked chip representing the solid-state imaging device according to Embodiment 1.
Figure 6:
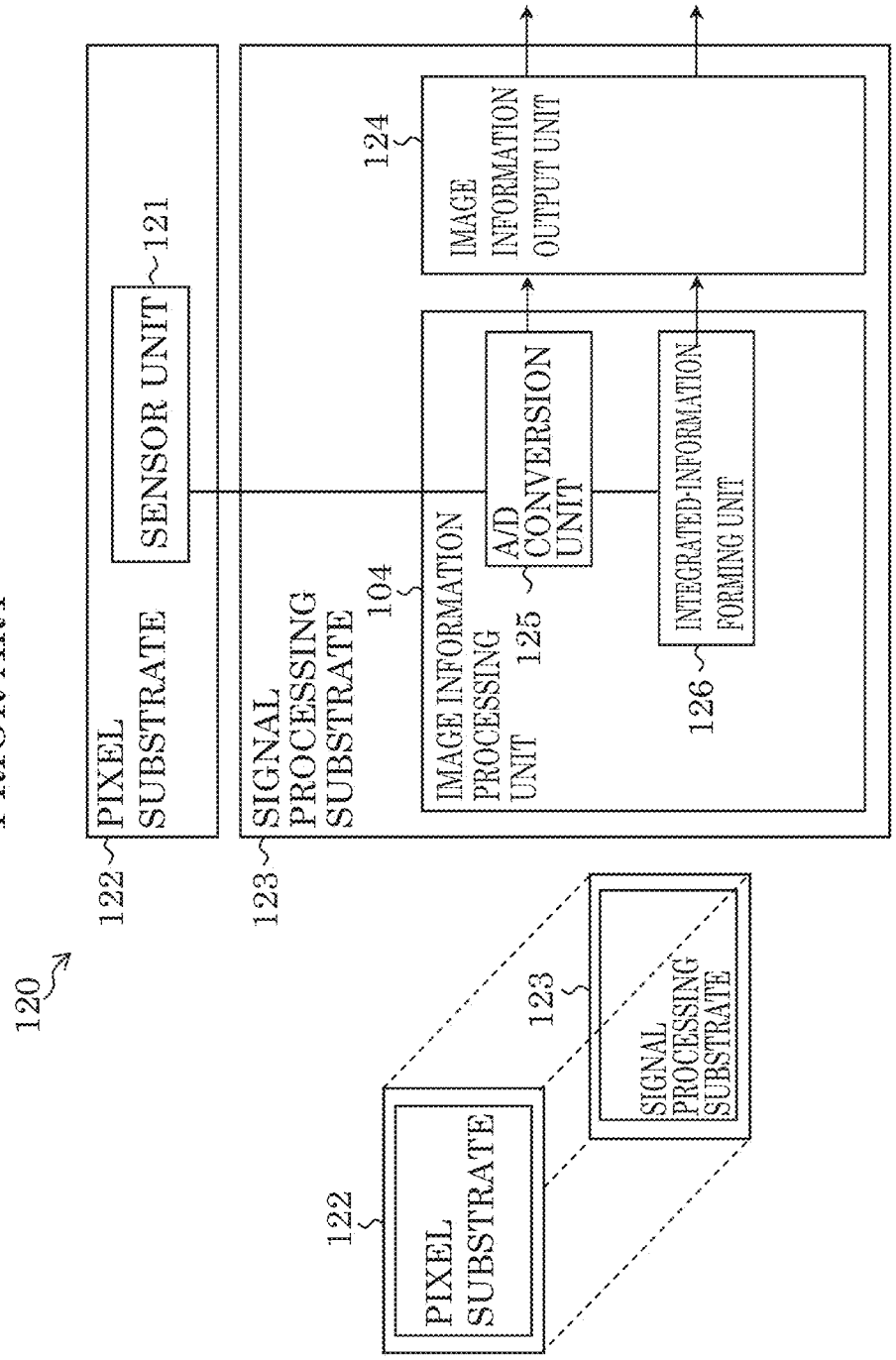
FIG. 6 is a block diagram of a configuration of a conventional solid-state imaging device.

FIG. 5A and FIG. 5B are each a cross-sectional view of an example of stacked chip representing solid-state imaging device 1 according to Embodiment 1. Solid-state imaging device 1 in FIG. 5A and FIG. 5B is a stack including first semiconductor substrate 1A stacked on and joined to second semiconductor substrate 1B.

Note that FIG. 5A is a structure in which light reaches photoelectric converter 61 from on a side where Cu wiring (metal wiring) 62 is formed, which is known as a front-side illumination (FSI) structure. However, solid-state imaging device 1 according to Embodiment 1 may use a structure as illustrated in FIG. 5B in which light reaches photoelectric converter 61 from on the side opposite to the side where Cu wiring (metal wiring) 62 is formed, which is known as a back-side illumination (BSI) structure.

In FIG. 5A and FIG. 5B, first semiconductor substrate 1A includes first silicon substrate 60, photoelectric converter 61, Cu wiring (metal wiring) 62, color filter 63, light collecting element 64, through electrode 65, and electrode pad 66. Photoelectric converter 61 is formed in first silicon substrate

60. On first silicon substrate 60, an SiO$_2$ film (oxide layer) is formed. Inside the SiO$_2$ film, Cu wiring 62 and other components are formed.

Second semiconductor substrate 1B includes second silicon substrate 50, transistor 51, Cu wiring 52, and memory element 53 of the nonvolatile memory. On second silicon substrate 50, an SiO$_2$ film is formed. Inside the SiO$_2$ film, for example, transistor 51, Cu wiring 52, and memory element 53 of nonvolatile memory 14 are formed.

First semiconductor substrate 1A and second semiconductor substrate 1B may be joined together using an adhesive (agent), or plasma activation joining by activating the surface of the substrate by plasma. In the present embodiment, the SiO$_2$ film formed on the surface of first semiconductor substrate 1A is joined to the SiO$_2$ film formed on the surface of second semiconductor substrate 1B by plasma activation joining. A process of plasma activation joining includes: flattening the surface of first semiconductor substrate 1A and the surface of second semiconductor substrate 1B by chemical mechanical polishing (CMP), for example; activating the surface of each substrate by plasma processing; and placing the surfaces to be joined together to face each other and performing annealing treatment at a temperature of from 200 degrees Celsius to 400 degrees Celsius to join the substrates. The annealing treatment is performed, for example, at a temperature of less than or equal to 400 degrees Celsius that does not affect the wiring, etc. However, the joining strength is weak at a temperature of less than or equal to 200 degrees Celsius.

As described above, light receiver 11 and image processing circuit 12 that processes a signal are separated, provided onto different semiconductor substrates, and joined together. This enables downsizing of solid-state imaging device 1. In addition, downsizing of solid-state imaging device 1 makes it possible to reduce the diameter of the scope of the endoscopic camera.

Furthermore, nonvolatile memory 14 of second semiconductor substrate 1B is formed on the joint surface side of first semiconductor substrate 1A. Therefore, it is difficult to physically analyze the use history data stored in nonvolatile memory 14. Furthermore, using a ferroelectric random access memory (FeRAM) or a resistive random access memory (ReRAM) as nonvolatile memory 14 makes it more difficult to physically analyze a change in a dielectric constant of the FeRAM or a change in a resistance value of the ReRAM. This prevents the data in nonvolatile memory 14 from being replaced with another data and secures the validity of the use history data.

The process of forming solid-state imaging device 1 usually greatly differs from the process of forming an FeRAM or an ReRAM. Therefore, it is difficult to form solid-state imaging device 1 and an FeRAM or an ReRAM on the same substrate. However, when first semiconductor substrate 1A and second semiconductor substrate 1B are separately formed and joined together, a solid-state imaging device equipped with an FeRAM or an ReRAM can be achieved.

In other words, for example, in a medical setting, when an endoscopic camera (camera scope 10) including solid-state imaging device 1 is used in a checkup or a surgery, a device to be used in such a checkup or a surgery need to be strictly asepticized or highly sterilized. After the device is used in a checkup or a surgery, components that contact a patient, such as an endoscope and its structural components, need to be asepticized by bringing to a high temperature with steam or by using a chemical agent. Such an endoscopic camera is expensive because the endoscopic camera needs to be resistant to high temperatures or chemical agents. Therefore, instead of using an expensive endoscopic camera, a packaged disposable endoscopic camera is demanded as a sterile product whose price can be reduced because such a disposable endoscopic camera does not need to be resistant to high temperatures or chemical agents used for repeated sterilization. Even in such a case, it is ensured that camera scope 10 is appropriately used as a disposable endoscopic camera and will not be reused.

In other words, solid-state imaging device 1 according to the embodiment of the present disclosure includes first semiconductor substrate 1A including light receiver 11 that receives incident light from the imaging optical system, and second semiconductor substrate 1B including image processing circuit 12 that processes a signal from light receiver 11. First semiconductor substrate 1A and second semiconductor substrate 1B are stacked and joined together. Second semiconductor substrate 1B includes a use history securing circuit that includes: nonvolatile memory 14; signal superimposing circuit 18; encryption circuit 15; input/output circuit 16; determination circuit 17; and blocking circuit 19. This configuration makes it possible to achieve solid-state imaging device 1 that is small; secures the use history; and ensures that the disposable image capturing device is appropriately used and will not be reused.

Furthermore, nonvolatile memory 14 stores, for example, image capturing device information; date and time of image capturing; and identification (ID) of the solid-state imaging device. This configuration secures the use history and the identification of the solid-state imaging device.

Furthermore, the information stored in nonvolatile memory 14 is encrypted as use history data by encryption circuit 15, and superimposed on the image signal by signal superimposing circuit 18. Furthermore, the use history data is superimposed on a part other than effective pixels in the image signal. Furthermore, the use history data may be superimposed as a digital watermark on a part in the effective pixels in the image signal. With this configuration, the image signal is output on which the encrypted ID, image capturing device information, and date and time of image capturing are superimposed. This makes it possible to prevent forgery or falsification of image data obtained by capturing a subject.

Furthermore, nonvolatile memory 14 of second semiconductor substrate 1B is formed on a joint surface side of first semiconductor substrate 1A. With this configuration, first semiconductor substrate 1A is on nonvolatile memory 14. Therefore, it is difficult to physically analyze the use history data stored in nonvolatile memory 14.

Furthermore, nonvolatile memory 14 may be an FeRAM or an ReRAM. This configuration makes it more difficult to physically analyze a change in a dielectric constant of the FeRAM or a change in a resistance value of the ReRAM. This prevents the data in nonvolatile memory 14 from being replaced with another data and secures the use history data.

As described above, the solid-state imaging device according to Embodiment 1 includes: first semiconductor substrate 1A including light receiver 11 that receives incident light; and second semiconductor substrate 1B including image processing circuit 12 that processes a signal from light receiver 11 and generates an image signal. Second semiconductor substrate 1B includes: nonvolatile memory 14 including a region in which use history data is stored; and control circuit 13 (use history securing circuit) that restricts output of the image signal when the use history data is stored in nonvolatile memory 14.

With this, the solid-state imaging device according to one aspect of the present disclosure is suitable for disposable use. For example, it is difficult to reuse the solid-state imaging device after being used once. In other words, the solid-state imaging device according to one aspect of the present disclosure ensures not to be reused.

Here, nonvolatile memory 14 may store, as the use history data, at least one of image capturing device information; date and time of image capturing; or identification (ID) of the solid-state imaging device, the image capturing device information indicating a device including the solid-state imaging device.

This makes it possible to prevent misdiagnosis due to referring to wrong image data obtained by capturing a subject, and also prevent forgery and falsification of the image data.

Here, control circuit 13 may include encryption circuit 15 that encrypts the use history data stored in nonvolatile memory 14, and signal superimposing circuit 18 that superimposes the encrypted use history data on the image signal.

Here, signal superimposing circuit 18 may superimpose the use history data on a part other than effective pixels in the image signal.

Here, signal superimposing circuit 18 may superimpose the use history data as a digital watermark on a part in effective pixels in the image signal.

Here, second semiconductor substrate 1B may include a joint surface to which first semiconductor substrate 1A is joined. Nonvolatile memory 14 is formed on a joint surface side of second semiconductor substrate 1B.

This makes it difficult to physically analyze the use history data stored in nonvolatile memory 14, and secures the validity of the use history data.

Here, nonvolatile memory 14 may be a ferroelectric random access memory (FeRAM) or a resistive random access memory (ReRAM).

This makes it more difficult to physically analyze a change in a dielectric constant of the FeRAM or a change in a resistance value of the ReRAM. This prevents the use history data from being replaced with another data and secures the validity of the use history data.

Here, control circuit 13 may include: determination circuit 17 that determines whether the use history data is present or absent in nonvolatile memory 14 in response to power being turned on; and blocking circuit 19 that restricts output of the image signal when determination circuit 17 determines that the use history data is present in nonvolatile memory 14.

This ensures that the solid-state imaging device will not be reused by blocking output of the image signal when the use history data is present.

Moreover, an endoscopic camera according to Embodiment 1 includes the solid-state imaging device described above.

With this, the endoscopic camera according to Embodiment 1 is suitable for disposable use. For example, it is difficult to reuse the endoscopic camera after being used once. In other words, this ensures that endoscopic camera will not be reused.

Although only an exemplary embodiment of the present disclosure has been described in detail above, those skilled in the art will readily appreciate that many modifications are possible in the exemplary embodiment without materially departing from the novel teachings and advantages of the present disclosure. Accordingly, all such modifications are intended to be included within the scope of the present disclosure.

INDUSTRIAL APPLICABILITY

The present disclosure is suitable for a solid-state imaging device and a camera (endoscopic camera), and industrially useful.

What is claimed is:

1. A solid-state imaging device, comprising:
a first semiconductor substrate including a light receiver that receives incident light; and
a second semiconductor substrate including an image processing circuit that processes a signal from the light receiver and generates an image signal, wherein
the second semiconductor substrate includes:
a nonvolatile memory including a region in which use history data is stored; and
a control circuit including a determination circuit, a blocking circuit, and an input/output circuit,
the determination circuit determines whether use history data is present in the nonvolatile memory in response to power being turned on, and
when the use history data is present, the blocking circuit prohibits output of the image signal from the input/output circuit.

2. The solid-state imaging device according to claim 1, wherein
the nonvolatile memory stores, as the use history data, at least one of: image capturing device information; date and time of image capturing.

3. The solid-state imaging device according to claim 1, wherein
the control circuit includes:
an encryption circuit that encrypts the use history data stored in the nonvolatile memory.

4. The solid-state imaging device according to claim 1, wherein
the second semiconductor substrate further includes a joint surface to which the first semiconductor substrate is joined, and
the nonvolatile memory is provided on a joint surface side of the second semiconductor substrate.

5. The solid-state imaging device according to claim 4, wherein
the nonvolatile memory is a ferroelectric random access memory (FeRAM) or a resistive random access memory (ReRAM).

6. An endoscopic camera, comprising:
the solid-state imaging device according to claim 1.

* * * * *